United States Patent

Yoshii et al.

[11] Patent Number: 5,449,667
[45] Date of Patent: Sep. 12, 1995

[54] AMIDOTHIOPHOSPHATE DERIVATIVE AND INSECTICIDE, NEMATOCIDE AND ACARICIDE CONTAINING THE SAME AS ACTIVE INGREDIENT

[75] Inventors: Yutaka Yoshii; Shigeru Saito, both of Toyonaka; Yoshikazu Itoh, Takarazuka; Mitsuru Sasaki, Nishinomiya, all of Japan

[73] Assignee: Sumitomo Chemical Company, Limited, Osaka, Japan

[21] Appl. No.: 286,448

[22] Filed: Aug. 5, 1994

[30] Foreign Application Priority Data

Aug. 10, 1993 [JP] Japan .................. 5-198220

[51] Int. Cl.$^6$ .................. A61K 31/66; C07F 9/24
[52] U.S. Cl. .................. 514/112; 558/168
[58] Field of Search .................. 558/168; 514/112

[56] References Cited

U.S. PATENT DOCUMENTS

| | | |
|---|---|---|
| 3,716,600 | 2/1973 | Magee . |
| 3,793,407 | 2/1974 | Stolzer et al. .................. 558/168 X |
| 3,845,172 | 10/1994 | Magee . |
| 3,898,260 | 8/1975 | Meyer et al. . |
| 4,544,553 | 10/1985 | Smolanoff et al. .................. 558/168 X |

FOREIGN PATENT DOCUMENTS

| | | |
|---|---|---|
| 0068823 | 1/1983 | European Pat. Off. . |
| 2198951 | 9/1973 | France . |
| 59-108796 | 6/1984 | Japan . |

OTHER PUBLICATIONS

*Chemical Abstracts* (1984) vol. 101:17 (Abstr. No. 152089), p. 737.

*Primary Examiner*—Robert W. Ramsuer
*Assistant Examiner*—Michael G. Ambrose
*Attorney, Agent, or Firm*—Birch, Stewart, Kolasch & Birch

[57] ABSTRACT

The present invention relates to an amidothiophosphate derivative represented by the formula II:

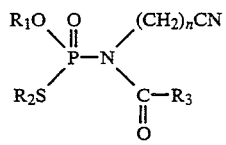

in which $R_1$ is a methyl group or an ethyl group; $R_2$ is a n-propyl group or a sec-butyl group; $R_3$ is a $C_1$-$C_4$ alkoxy group, a $C_1$-$C_4$ alkylthio group, phenyl group or a phenoxy group; and n represents 1 or 2, and an insecticide, a nematocide and an acaricide containing the same as an active ingredient.

5 Claims, No Drawings

AMIDOTHIOPHOSPHATE DERIVATIVE AND INSECTICIDE, NEMATOCIDE AND ACARICIDE CONTAINING THE SAME AS ACTIVE INGREDIENT

FIELD OF THE INVENTION

The present invention relates to an amidothiophosphate derivative, and an insecticide, a nematocide and an acaricide containing the amidothiophosphate derivative as an active ingredient.

DESCRIPTION OF THE RELATED ART

Several amidothiophosphate derivatives are known to have activities for controlling noxious insects, nematodes and mites. For example, Japanese Patent Kokai No. 59-108796 discloses an amidothiophosphate derivative represented by the formula I:

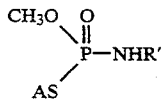

wherein A represents a n-propyl group, an isobutyl group or a sec-butyl group; and R' represents a methyl group or an ethyl group.

The amidothiophosphate derivative of the formula I, however, has rather high acute toxicity to mammals and thereby cannot be practically used as an active ingredient of insecticides, nematocides and acaricides.

SUMMARY OF THE INVENTION

To overcome the drawbacks of said compounds, the inventors have conducted extensive studies and found that the amidothiophosphate derivative (hereinafter referred to as the present compound) of the formula II shown below has excellent activities for controlling noxious insects, nematodes and mites while having low acute toxicity to mammals.

Thus the present invention provides an amidothiophosphate derivative represented by the formula II:

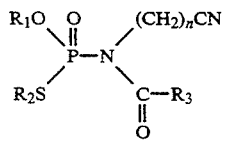

wherein $R_1$ is a methyl group or an ethyl group; $R_2$ is a n-propyl group or a sec-butyl group; $R_3$ is a $C_1$-$C_4$ alkylthio group, a phenyl group, a $C_1$-$C_4$ alkoxy group or a phenoxy group; and n represents 1 or 2.

The invention also provides an insecticide, a nematocide and an acaricide containing the amidothiophosphate derivative of the formula II as an active ingredient, and a method of controlling insects, nematodes or acarines which comprises applying the compound II as an active ingredient to the locus where pests propagate.

DESCRIPTION OF THE PREFERRED EMBODIMENT

The present compound exerts excellent insecticidal, nematocidal and acaricidal activities against noxious insects of Lepidoptera such as *Chilo suppressalis* and *Spodoptera litura*, those of Diptera such as *Culex pipiens pallens* and *Musca domestica* (house fly), nematodes such as *Meloidogyne incognita*, and mites such as *Tetranychus cinnabarinus*. The compound is especially active against noxious insects and nematodes in soil which damage a variety of agricultural products, flowers and grass.

Table 1 shows examples of the compound (Substituents of the compound of the formula II are listed.).

TABLE 1

| $R_1$ | $R_2$ | $R_3$ | n |
|---|---|---|---|
| $CH_3$ | $nC_3H_7$ | $C_6H_5$ | 1 |
| $CH_3$ | $nC_3H_7$ | $C_6H_5$ | 2 |
| $CH_3$ | $nC_3H_7$ | $OCH_3$ | 1 |
| $CH_3$ | $nC_3H_7$ | $OC_2H_5$ | 1 |
| $CH_3$ | $nC_3H_7$ | $OC_3H_7$-i | 1 |
| $CH_3$ | $nC_3H_7$ | $OC_3H_7$-n | 1 |
| $CH_3$ | $nC_3H_7$ | $OC_4H_9$-n | 1 |
| $CH_3$ | $nC_3H_7$ | $OC_4H_9$-i | 1 |
| $CH_3$ | $nC_3H_7$ | $OC_4H_9$-s | 1 |
| $CH_3$ | $nC_3H_7$ | $OC_4H_9$-t | 1 |
| $CH_3$ | $nC_3H_7$ | $OCH_3$ | 2 |
| $CH_3$ | $nC_3H_7$ | $OC_2H_5$ | 2 |
| $CH_3$ | $nC_3H_7$ | $OC_3H_7$-i | 2 |
| $CH_3$ | $nC_3H_7$ | $OC_3H_7$-n | 2 |
| $CH_3$ | $nC_3H_7$ | $OC_4H_9$-n | 2 |
| $CH_3$ | $nC_3H_7$ | $OC_4H_9$-s | 2 |
| $CH_3$ | $nC_3H_7$ | $OC_4H_9$-t | 2 |
| $CH_3$ | $nC_3H_7$ | $SCH_3$ | 1 |
| $CH_3$ | $nC_3H_7$ | $SC_2H_5$ | 1 |
| $CH_3$ | $nC_3H_7$ | $SC_3H_7$-i | 1 |
| $CH_3$ | $nC_3H_7$ | $SC_3H_7$-n | 1 |
| $CH_3$ | $nC_3H_7$ | $SC_4H_9$-n | 1 |
| $CH_3$ | $nC_3H_7$ | $SC_4H_9$-i | 1 |
| $CH_3$ | $nC_3H_7$ | $SC_4H_9$-s | 1 |
| $CH_3$ | $nC_3H_7$ | $SC_4H_9$-t | 1 |
| $CH_3$ | $nC_3H_7$ | $SCH_3$ | 2 |
| $CH_3$ | $nC_3H_7$ | $SC_2H_5$ | 2 |
| $CH_3$ | $nC_3H_7$ | $SC_3H_7$-i | 2 |
| $CH_3$ | $nC_3H_7$ | $SC_3H_7$-n | 2 |
| $CH_3$ | $nC_3H_7$ | $SC_4H_9$-n | 2 |
| $CH_3$ | $nC_3H_7$ | $SC_4H_9$-i | 2 |
| $CH_3$ | $nC_3H_7$ | $SC_4H_9$-s | 2 |
| $CH_3$ | $nC_3H_7$ | $SC_4H_9$-t | 2 |
| $CH_3$ | $nC_3H_7$ | $C_6H_5O$ | 1 |
| $CH_3$ | $nC_3H_7$ | $C_6H_5O$ | 2 |
| $C_2H_5$ | $nC_3H_7$ | $C_6H_5$ | 1 |
| $C_2H_5$ | $nC_3H_7$ | $C_6H_5$ | 2 |
| $C_2H_5$ | $nC_3H_7$ | $OCH_3$ | 1 |
| $C_2H_5$ | $nC_3H_7$ | $OC_2H_5$ | 1 |
| $C_2H_5$ | $nC_3H_7$ | $OC_3H_7$-i | 1 |
| $C_2H_5$ | $nC_3H_7$ | $OC_3H_7$-n | 1 |
| $C_2H_5$ | $nC_3H_7$ | $OC_4H_9$-n | 1 |
| $C_2H_5$ | $nC_3H_7$ | $OC_4H_9$-i | 1 |
| $C_2H_5$ | $nC_3H_7$ | $OC_4H_9$-s | 1 |
| $C_2H_5$ | $nC_3H_7$ | $OC_4H_9$-t | 1 |
| $C_2H_5$ | $nC_3H_7$ | $OCH_3$ | 2 |
| $C_2H_5$ | $nC_3H_7$ | $OC_2H_5$ | 2 |
| $C_2H_5$ | $nC_3H_7$ | $OC_3H_7$-i | 2 |
| $C_2H_5$ | $nC_3H_7$ | $OC_3H_7$-n | 2 |
| $C_2H_5$ | $nC_3H_7$ | $OC_4H_9$-n | 2 |
| $C_2H_5$ | $nC_3H_7$ | $OC_4H_9$-s | 2 |
| $C_2H_5$ | $nC_3H_7$ | $OC_4H_9$-t | 2 |
| $C_2H_5$ | $nC_3H_7$ | $SCH_3$ | 1 |
| $C_2H_5$ | $nC_3H_7$ | $SC_2H_5$ | 1 |
| $C_2H_5$ | $nC_3H_7$ | $SC_3H_7$-i | 1 |
| $C_2H_5$ | $nC_3H_7$ | $SC_3H_7$-n | 1 |
| $C_2H_5$ | $nC_3H_7$ | $SC_4H_9$-n | 1 |
| $C_2H_5$ | $nC_3H_7$ | $SC_4H_9$-i | 1 |
| $C_2H_5$ | $nC_3H_7$ | $SC_4H_9$-s | 1 |
| $C_2H_5$ | $nC_3H_7$ | $SC_4H_9$-t | 1 |
| $C_2H_5$ | $nC_3H_7$ | $SCH_3$ | 2 |
| $C_2H_5$ | $nC_3H_7$ | $SC_2H_5$ | 2 |
| $C_2H_5$ | $nC_3H_7$ | $SC_3H_7$-i | 2 |
| $C_2H_5$ | $nC_3H_7$ | $SC_3H_7$-n | 2 |
| $C_2H_5$ | $nC_3H_7$ | $SC_4H_9$-n | 2 |
| $C_2H_5$ | $nC_3H_7$ | $SC_4H_9$-i | 2 |
| $C_2H_5$ | $nC_3H_7$ | $SC_4H_9$-s | 2 |
| $C_2H_5$ | $nC_3H_7$ | $SC_4H_9$-t | 2 |
| $C_2H_5$ | $nC_3H_7$ | $C_6H_5O$ | 1 |
| $C_2H_5$ | $nC_3H_7$ | $C_6H_5O$ | 2 |
| $CH_3$ | $sC_4H_9$ | $C_6H_5$ | 1 |
| $CH_3$ | $sC_4H_9$ | $C_6H_5$ | 2 |

TABLE 1-continued

| R₁ | R₂ | R₃ | n |
|---|---|---|---|
| $CH_3$ | $sC_4H_9$ | $OCH_3$ | 1 |
| $CH_3$ | $sC_4H_9$ | $OC_2H_5$ | 1 |
| $CH_3$ | $sC_4H_9$ | $OC_3H_7$-i | 1 |
| $CH_3$ | $sC_4H_9$ | $OC_3H_7$-n | 1 |
| $CH_3$ | $sC_4H_9$ | $OC_4H_9$-n | 1 |
| $CH_3$ | $sC_4H_9$ | $OC_4H_9$-i | 1 |
| $CH_3$ | $sC_4H_9$ | $OC_4H_9$-s | 1 |
| $CH_3$ | $sC_4H_9$ | $OC_4H_9$-t | 1 |
| $CH_3$ | $sC_4H_9$ | $OCH_3$ | 2 |
| $CH_3$ | $sC_4H_9$ | $OC_2H_5$ | 2 |
| $CH_3$ | $sC_4H_9$ | $OC_3H_7$-i | 2 |
| $CH_3$ | $sC_4H_9$ | $OC_3H_7$-n | 2 |
| $CH_3$ | $sC_4H_9$ | $OC_4H_9$-n | 2 |
| $CH_3$ | $sC_4H_9$ | $OC_4H_9$-i | 2 |
| $CH_3$ | $sC_4H_9$ | $OC_4H_9$-s | 2 |
| $CH_3$ | $sC_4H_9$ | $OC_4H_9$-t | 2 |
| $CH_3$ | $sC_4H_9$ | $SCH_3$ | 1 |
| $CH_3$ | $sC_4H_9$ | $SC_2H_5$ | 1 |
| $CH_3$ | $sC_4H_9$ | $SC_3H_7$-i | 1 |
| $CH_3$ | $sC_4H_9$ | $SC_3H_7$-n | 1 |
| $CH_3$ | $sC_4H_9$ | $SC_4H_9$-n | 1 |
| $CH_3$ | $sC_4H_9$ | $SC_4H_9$-i | 1 |
| $CH_3$ | $sC_4H_9$ | $SC_4H_9$-s | 1 |
| $CH_3$ | $sC_4H_9$ | $SC_4H_9$-t | 1 |
| $CH_3$ | $sC_4H_9$ | $SCH_3$ | 2 |
| $CH_3$ | $sC_4H_9$ | $SC_2H_5$ | 2 |
| $CH_3$ | $sC_4H_9$ | $SC_3H_7$-n | 2 |
| $CH_3$ | $sC_4H_9$ | $SC_4H_9$-n | 2 |
| $CH_3$ | $sC_4H_9$ | $SC_4H_9$-i | 2 |
| $CH_3$ | $sC_4H_9$ | $C_6H_5O$ | 1 |
| $CH_3$ | $sC_4H_9$ | $C_6H_5O$ | 2 |
| $C_2H_5$ | $sC_4H_9$ | $C_4H_9$-n | 1 |
| $C_2H_5$ | $sC_4H_9$ | $OCH_3$ | 1 |
| $C_2H_5$ | $sC_4H_9$ | $OC_2H_5$ | 1 |
| $C_2H_5$ | $sC_4H_9$ | $OC_3H_7$-i | 1 |
| $C_2H_5$ | $sC_4H_9$ | $OC_3H_7$-n | 1 |
| $C_2H_5$ | $sC_4H_9$ | $OC_4H_9$-n | 1 |
| $C_2H_5$ | $sC_4H_9$ | $OC_4H_9$-i | 1 |
| $C_2H_5$ | $sC_4H_9$ | $OC_4H_9$-s | 1 |
| $C_2H_5$ | $sC_4H_9$ | $OC_4H_9$-t | 1 |
| $C_2H_5$ | $sC_4H_9$ | $OCH_3$ | 2 |
| $C_2H_5$ | $sC_4H_9$ | $OC_2H_5$ | 2 |
| $C_2H_5$ | $sC_4H_9$ | $OC_3H_7$-i | 2 |
| $C_2H_5$ | $sC_4H_9$ | $OC_3H_7$-n | 2 |
| $C_2H_5$ | $sC_4H_9$ | $OC_4H_9$-n | 2 |
| $C_2H_5$ | $sC_4H_9$ | $SCH_3$ | 1 |
| $C_2H_5$ | $sC_4H_9$ | $SC_2H_5$ | 1 |
| $C_2H_5$ | $sC_4H_9$ | $SC_3H_7$-n | 1 |
| $C_2H_5$ | $sC_4H_9$ | $SC_4H_9$-n | 1 |
| $C_2H_5$ | $sC_4H_9$ | $SCH_3$ | 2 |
| $C_2H_5$ | $sC_4H_9$ | $SC_2H_5$ | 2 |
| $C_2H_5$ | $sC_4H_9$ | $SC_3H_7$-n | 2 |
| $C_2H_5$ | $sC_4H_9$ | $SC_4H_9$-n | 2 |
| $C_2H_5$ | $sC_4H_9$ | $C_6H_5O$ | 1 |
| $C_2H_5$ | $sC_4H_9$ | $C_6H_5O$ | 2 |

The present compound is produced by the following methods.

Method A

A method of producing the compound of the formula II which comprises reacting a phosphoric acid chloride of the formula III:

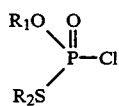

III wherein R₁ and R₂ are the same as defined above, with a nitrile derivative of the formula IV:

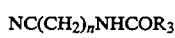       IV wherein R₃ and n are the same as defined above, in the presence of a base.

The reaction is usually carried out in a solvent. Examples of the solvent are an ether such as diethyl ether or tetrahydrofuran, and an aromatic hydrocarbon such as benzene or toluene.

The base to be used is an alkaline metal hydride, such as sodium hydride or potassium hydride.

The reaction temperature is usually from −70° C. to 100° C. or a refluxing temperature of the solvent. The amount of the phosphoric acid chloride of the formula III is usually 1 to 1.2 moles and the amount of the base to be used is 1 to 1.2 moles to 1 mole of the nitrile derivative of the formula IV.

The phosphoric acid chloride of the formula III is produced, for example, by the method described in 'Methoden der Organischen Chemie' (Houben-Weyl, Band E2, pp 542–543 (1982)).

The nitrile derivative of the formula IV is produced, for example, by the method described in 'Beilstein Handbuch' (Vol. 4, p 363).

Method B

A method of producing the present compound II which comprises reacting the amidothiophosphate of the formula V:

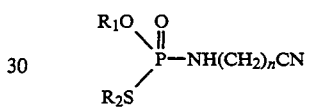     V wherein R₁, R₂ and n are the same as defined above, with an acid chloride of the formula VI:

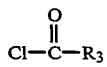     IV wherein R₃ is the same as defined above, in the presence of a base.

The reaction is generally carried out in a solvent. Examples of the solvent include an ether such as diethyl ether or tetrahydrofuran, and an aromatic hydrocarbon such as benzene or toluene. The base to be used is an alkaline metal hydride such as sodium hydride or potassium hydride. The reaction temperature is usually −70° C. to 100° C. or a refluxing temperature of the solvent. The amount of the acid chloride of the formula VI is usually from 1 to 1.2 moles and that of the base to be used is usually 1 to 1.2 moles to 1 mole of the amidothiophosphate of the formula V.

The amidothiophosphate of the formula V is produced by reacting the phosphoric acid chloride of the formula III with aminoacetonitrile or its salt (for example, an inorganic salt such as hydrochloride or sulfate) or 2-aminopropionitrile or its salt (for example, an inorganic salt such as hydrochloride or sulfate) in the presence of a base in an organic solvent, water, or a mixture of an organic solvent and water. Examples of the organic solvent to be used include ethers such as diethyl ether and diisopropyl ether, halogenated hydrocarbons such as methylene chloride and chloroform, and aromatic hydrocarbons such as benzene and toluene. Examples of the base include tertiary amines such as pyridine and triethylamine, inorganic bases such as sodium hydroxide, potassium hydroxide, sodium carbonate and potassium carbonate. The amount of the phosphoric acid chloride of the formula III to be used is usually 1 to 1.2 moles and the amount of the base is 1 to 1.2 moles, to 1 mole of aminoacetonitrile (or its salt) or 2-aminopropionitrile (or its salt).

In both of the method A and method B, after completion of the reaction, the present compound is isolated by a conventional post-treatment such as solvent extraction and/or concentration. The compound obtained may be purified by column chromatography, distillation, or the like if necessary.

The compound of the present invention is effective for controlling noxious insects, mites and nematodes listed below:

Hemiptera

Delphacidae (leaf hoppers) such as *Laodelphax striatellus, Nilaparvata lugens* and *Sogatella furcifera;* Cicadelloidea (leaf hoppers) such as *Nephotettix cincticeps* and *Nephotettix virescens,* Aphidoidea (aphids), Pentatomidae (stink bugs), Aleyrodidae, Coccoidea (scale insects), Tingidae (lace bugs), Psyllidae (jumping plantlices), etc.;

Lepidoptera

Pyralidae such as *Chilo suppressalis, Cnaphalocrocis medinalis, Ostrinia nubilalis, Parapediasia teterrella, Notarcha derogata* and *Plodia interpunctella,* Noctuidae (owlet moths) such as *Spodoptera litura, Pseudaletia separata, Mamestra brassicae, Agrotis ipsilon,* Heliothis moths, Helicoverpa moths, Pieridae such as *Pieris rapae crucivora,* Tortricidae (bell moths) such as *Grapholita molesta* and *Cydia pomonella, Carposina niponensis,* Lyonetiidae (leaf mining moths), Euproctis and Lymantria (gypsy) moths, Yponomeutidae such as *Plutella xylostella,* Gelechiidae such as *Pectinophora gossypiella,* Arctiidae such as *Hydhantria cunea, Tinea translucens, Tineola bisselliella,* etc.;

Diptera

Culex (house mosquitos) such as *Culex pipiens pallens* and *Culex tritaeniorhynchus,* Aedes such as *Aedes albopictus* and *Aedes aegypti,* Anophelinae such as *Anophelinae sinensis,* Chironomidae (midges), Muscidae such as *Musca domestica* (house fly) and *Muscina stabulans,* Calliphoridae (blow flies), Sarcophagidae (flesh flies), Anthomyiidae such as Delia Platura and *Delia antigua,* Trypetidae (fruit flies), Drosophilidae (wine flies), Psychodidae (moth flies), Tabanidae (deer flies), Simuliidae (black flies), Stomoxyinae, Agromyzidae (leaf miner flies) etc.;

Coleoptera (Beetles)

Diabrotica (corn rootworms) such as *Diabrotica virgifera* and *Diabrotica undecimpunctata,* Scarabaeidae such as *Anomala cuprea* and *Anomala rufocuprea,* Curculionidae (snout beetles) such as *Sitophilus zeamais* (grain weevils), *Lissorphoptrus oryzophilus, Hypera pastica,* and *Calosobruchys chinensis, Neatus ventralis* (darkling beetles) such as *Tenebrio molitor* and *Tribolium castaneum,* Chrysomelidae (leaf beetles) such as *Aulacophora femoralis, Leptinotarsa decemlineata* and *Phyllotreta striolata,* Anobiidae (death-watch beetles), Epilachna spp. such as *Henosepilachna vigintioctopunctata,* Lyctidae (powder-post beetles), Bostrychidae (lesser grain borers), *Paederus fuscipes,* etc.;

Blattaria (Cockroaches)

*Blattella germanica* (croton bugs), *Periplaneta fuliginosa, Periplaneta americana, Periplaneta brunnea, Blatta orientalis,* etc.;

Thysanoptera (Thrips)

*Thrips palmi, Thrips tabaci, Thrips hawaiiensis,* etc.;

Hymenoptera

Formicidae (ants), Vespa (hornets), Bethylidae (bethylidwasps), Tenthredinoidae (sawflies) such as *Athalia rosae japonensis* (cabbage sawfly), etc.;

Orthoptera

Gryllotalpha (mole crickets), Acridoidea (grasshoppers), etc.;

Siphonaptera (Fleas)

*Purex irritans,* etc.;

Anoplura (Sucking Louses)

*Pediculus humanus capitis, Phthirus pubis,* etc.;

Isoptera (Termites)

*Reticulitermes speratus, Coptotermes formosanus,* etc.;

Mites

Tetranychidae (spider mites) such as *Tetranychus cinnabarinus, Tetranychus urticae, Tetranychus kanzawai, Panonychus citri* and *Panonychus ulmi,* Eriophyidae such as *Aculops pelekassi* and *Calacarus carinatus,* Tarsonemidae such as *Polyphaqotarsonemus latus,* Tenuipalpidae, Tuckerellidae, Ixodidae (ticks) such as *Boophilus microplus,* Acaridae, Pyroglyphidae, Cheyletidae, Dermanyssidae, etc.;

Nematoda (Nematodes)

Tylenchida, Pratylenchidae such as *Pratylenchus coffeae, Pratylenchus penetrans, Pratylenchus loosi* and *Pratylenchus vulnus,* Heteroderidae such as *Heterodera glycines* and *Globodera rostochiensis,* Meloidogynidae such as *Meloidogyne hapla* and *Meloidogyne incognita.*

For the practical use of the present compound as an active ingredient of an insecticide, an acaricide, or a nematocide, it may be used as it is, however, the present compound is usually formulated into oil solutions, emulsifiable concentrates, wettable powders, flowables such as water-based suspensions and water-based emulsions, granules, dusts, aerosols, heating fumigants such as combustible fumigants, chemical fumigants and porous ceramics fumigants, ULV formulations and poison baits. These formulations are usually prepared by mixing the present compound with a solid carrier, a liquid carrier, a gaseous carrier or a bait, and a surfactant and other auxiliaries for formulations may be added thereto if necessary. These formulations usually contain the present compounds as an active ingredient in an amount of 0.01% to 95% by weight.

Examples of the solid carriers to be used for the formulations include fine powders or granules of clays such as kaolin clay, diatomaceous earth, synthetic hydrated silicon oxide, bentonite and acid clay; talcs; ceramics; other inorganic minerals such as sericite, quartz, sulfur, active carbon, calcium carbonate and hydrated silica; and chemical fertilizers such as ammonium sulfate, ammonium phosphate, ammonium nitrate, urea and ammonium chloride. Examples of the liquid carrier include water, alcohols such as methanol and ethanol; ketones such as acetone and methyl ethyl ketone; aromatic hydrocarbons such as benzene, toluene, xylene, ethylbenzene and methylnaphthalene; aliphatic hydrocarbons such as hexane, cyclohexane, kerosine and gas oil; esters such as ethyl acetate and butyl acetate; nitriles such as acetonitrile and isobutyronitrile; ethers such as diisopropyl ether and dioxane; acid amides such as N,N-dimethylformamide and N,N-dimethylacetamide; halogenated hydrocarbons such as dichloromethane, trichloroethane and carbon tetrachloride; dimethyl sulfoxide; vegetable oils such as soybean oil and cotton seed oil. Examples of the gaseous carrier or propellant include CFCs (chlorofluorocarbons), butane gas, LPG (liquefied petroleum gas), dimethyl ether, and carbon dioxide.

Examples of the surfactant includes alkyl sulfates, alkyl sulfonates, alkyl arylsulfonates, alkyl aryl ethers, polyoxyethylene compounds thereof, polyethylene glycol ethers, polyhydric alcohol derivatives, and sugar alcohol derivatives.

Examples of the auxiliaries for the formulations, such as fixing agents or dispersing agents include casein, gelatin, polysaccharides such as starch, gum arabic, cellulose derivatives and alginic acid, lignin derivatives, bentonite, sugars, and synthetic water-soluble polymers such as polyvinyl alcohol, polyvinyl pyrrolidone and polyacrylic acid. Examples of the stabilizer include PAP (isopropyl acid phosphate), BHT (2,6-di-t-butyl-4-methylphenol), BHA (mixture of 2-t-butyl-4-methoxyphenol and 3-t-butyl-4-methoxyphenol), vegetable oils, mineral oils, surfactants, fatty acids and esters of fatty acids.

The base material of the combustible fumigant includes, for example, an exothermic agent such as a nitrate, a nitrite, a guanidine salt, potassium chlorate, nitrocellulose, ethylcellulose or wood powder; a pyrolytic stimulating agent such as an alkaline metal salt, an alkaline earth metal salt, a dichromate, or a chromate; an oxygen source such as potassium nitrates; a combustion assistant such as melamine or wheat starch; a bulk filler such as diatomaceous earth; and a binding agent such as synthetic glue.

The base material of the chemical fumigant includes, for example, an exothermic agent such as an alkaline metal sulfide, a polysulfide, a hydrosulfide, a hydrated salt or calcium oxide; a catalytic agent such as a carbonaneous substance, iron carbide or active clay; an organic foaming agent such as azodicarbonamide, benzenesulfonylhydrazide, N,N'-dinitrosopentamethylenetetramine, polystyrene or polyurethane; and a filler such as natural and synthetic fibers.

The base material of the poison baits includes a bait material such as grain powder, purified vegetable oil, sugar or crystalline cellulose, an antioxidant such as dibutylhydroxytoluene or nordihydroguaiaretic acid, a preservative such as dehydroacetic acid, a substance for preventing erroneous eating such as red pepper powder, an attractant flavor such as cheese flavor or onion flavor.

The flowables such as the water-based suspensions and water-based emulsions are usually obtained by finely dispersing the present compound in an amount of 1 to 75% in water containing a 0.5 to 15% dispersing agent, a 0.1 to 10% suspension assistant (for example, protective colloid or a compound giving thixotropy), and 0 to 10% additives (for example, an antifoamer, a stabilizer, a bactericide, a rust preventive agent, an antimold, a developing agent, a penetrating assistant or an antifreezing agent). The present compound may be dispersed in oil, in which the present compound is substantially insoluble, to form oil suspensions. Examples of the protective colloid include casein, gelatin, gums, cellulose ethers and polyvinyl alcohol. The compound giving thixotropy may be bentonite, aluminum magnesium silicate, xanthan gum or polyacrylic acid.

The formulations thus obtained may be used as prepared or used after diluting with water. The formulations of the present invention may also be used in a simultaneously with other insecticides, acaricides, nematocides, bactericides, herbicides, plant growth regulators, synergists, fertilizers and/or soil conditioners under non-mixed conditions or pre-mixed conditions.

Insecticides, acaricides and/or nematocides to be used include organophosphorous compounds such as Fenitrothion [(O,O-dimethyl O-(3-methyl-4-nitrophenyl)phosphorothionate], Fenthion [O,O-dimethyl O-(3-methyl-4-methylthiophenyl)phophorothionate], Diazinon (Dimpylate) [O,O-diethyl-O-2-isopropyl-6-methylpyrimidin- 4-ylphosphorothioate], Chlorpyriphos [O,O-dimethyl-O-3,5,6-trichloro-2-pyridylphosphorothioate], Acephate [O,S-dimethyl acetylphosphoramidothioate], Methidachion (DMTP) [S-2,3-dihydro-5-methoxy-2-oxo-1,3,4-thiadiazol-3-ylmethyl O,O-dimethylphosphorothiolothionate], Disulfoton [O,O-diethyl S-2-ethylthioethyl phosphorothiolothionate], Dichlorvos (DDVP) [2,2-dichlorovinyl dimethylphosphate], Sulprofos [O-ethyl O-4-methylthiophenyl S-propylphosphorodithioate], Cyanophos [O-4-cyanophenyl-O,O-dimethylphosphorothioate], Dioxabenzofos [2-methoxy-4H-1,3,2-benzodioxaphosphorin-2-sulfide], Dimethoate [O,O-dimethyl-S-(N-methylcarbamoylmethyl)phosphorodithioate], Phenthoate [S-ethoxycarbonylbenzyldimethyl phosphorothiolothionate], Malathion [1,2-bis(ethoxylcarbonyl)ethyl O,O-dimethyl phosphorothiolothionate], Trichlorfon (Metrifonate) [dimethyl 2,2,2-trichloro-1-hydroxyethyl phosphonate], Azinphosmethyl [S-(3,4-dihydro-4-oxo-1,2,3-benzotriazine-3-ylmethyl)dimethyl phosphorothiolothionate], Monocrotophos [cis-3-(dimethoxyphosphinyloxy)-N-methylcrotonamide], and Ethion [S,S'-methylenebis(phosphorothiolothionate)].

Other examples are carbamate compounds such as BPMC [2-sec-butylphenyl methyl carbamate], Benfuracarb [ethyl N-(2,3-dihydro-2,2-dimethylbenzofuran-7-yloxycarbonyl (methyl)aminothio)-N-isopropyl-B-alaninate], Propoxur (PHC) [2-isopropoxyphenyl N-methyl carbamate], Carbosulfan [2,3-dihydro-2,2-dimethyl-7-benzo[b]furanyl N-dibutylaminothio-N-methyl carbamate], Carbaril [1-naphthyl N-methylcarbamate], Methomyl [S-methyl-N-((methylcarbamoyl)oxy)thioacetoimidate], methyl-N-((methylcarbamoyl)oxy)thioacetoimidate], Ethiofencarb [2-(ethylthiomethyl)phenyl methylcarbamate], Aldicarb [2-methyl-2-(methylthio)propanol O-((methylamino)carbonyl)oxime], Oxamyl [N,N-dimethyl 2-methylcarbamoyloxyimino-2-(methylthio)acetamide] and Fenothiocarb [S-4-phenoxybutyl)-N,N-dimethylthiocarbamate].

Other examples include pyrethroid compounds such as Etofenprox [2-(4-ethoxyphenyl)-2-methylpropyl-3-phenoxybenzyl ether], Fenvalerate [(RS)-α-cyano-3-phenoxybenzyl (RS)-2-(4-chlorophenyl)-3-methylbutyrate], S-Fenvalerate [(S)-α-cyano-3-phenoxybenzyl (S)-2-(4-chlorophenyl)-3-methylbutyrate], Fenpropathrin [(RS)-α-cyano-3-phenoxybenzyl 2,2,3,3-tetramethylcyclopropanecarboxylate], Cypermethrin [(RS)-α-cyano- 3-phenoxybenzyl (1RS,3RS)-3-(2,2-dichlorovinyl)-2,2-dimethylcyclopropanecarboxylate], Permethrin [3-phenoxybenzyl (1RS,3RS)-3-(2,2-dichlorovinyl)-2,2-dimethylcyclopropanecarboxylate], Cyhalothrin [(RS)-α-cyano-3phenoxybenzyl (Z)-(1RS)-cis-3-(2-chloro-3,3,3-trifluoropropen-1-yl)-2,2-dimethylcyclopropanecarboxylate], Deltamethrin [(S)-α-cyano-3-phenoxybenzyl (1R, 3R)-3-(2,2-dibromovinyl)-2,2-dimethylcyclopropanecarboxylate], Cycloprothrin [(RS)-α-cyano-3phenoxybenzyl (RS)-2,2-dichloro-1-(4-ethoxyphenyl)-cyclopropanecarboxylate], Fluvalinate [α-cyano-3-phenoxybenzyl N-(2-chloro-α,α,α-trifluoro-p-tolyl)-D-valinate], Bifenthrin [2-methylbiphenyl-2-ylmethyl)(Z)-(1RS)-cis-3-(2-chloro-3,3,3-trifluoropropen-1-yl)2,2-dimethylcyclopropanecarboxylate], Acrinathrin [(S)-(α)-cyano-(3-phenoxyphenyl)-methyl (1R)-(1α(S*), 3αZ))-2,2-dimethyl-3-(3-oxo-3-(2,2,2-trifluoro-1-(trifluoromethyl)ethoxy-1-propenyl)-cyclopropanecarboxylate], 2-methyl-2-(4-bromodifluoromethoxyphenyl)propyl (3-phenoxybenzyl) ether, Traromethrin [(S)-α-cyano-3-phenoxylbenzyl (1R,3R)-3-((1'RS)(1',1',2',2'-tetrabromo-ethyl))-2,2-dimethylcyclopropanecarboxylate] and Silafluofen [4-ethoxylphenyl(3-(4-fluoro-3-phenoxyphenyl)propyl)dimethylsilane].

Other examples include thiadiazine derivatives such as Buprofezin [2-t-butylimino-3-isopropyl-5-phenyl-1,3,5-thiadiazin-4-one], nitroimidazolidine derivatives such as Imidacloprid [1-(6-chloro-3-pyridylmethyl)-N-nitroimidazolidin-2-ylidenamine], Cartap [S,S'-(2-dimethylaminotrimethylene)bisthiocarbamate], Thiocyclam [N,N-dimethyl-1,2,3-trithian-5-ylamine], Bensultap [S,S'-2-dimethylaminotrimethylene di(benzenethiosulfonate)], N-cyanoamidine derivatives such as N-cyano-N'-methyl-N'-(6-chloro-3-pyridylmethyl)acetoamidine, chlorinated hydrocarbons such as Endosulfan [6,7,8,9,10,10-hexachloro-1,5,5a,6,9,9a-hexahydro-6,9-methanobenzo [e]-2,4,3-dioxathiepin 3-oxide], γ-BHC [1,2,3,4,5,6-hexachlorocyclohexane], 1,1-bis(chlorophenyl)- 3,3,3-trichloroethanol, benzoylphenylurea compounds such as Chlorofluazuron [1-(3,5-dichloro-4-(3-chloro-5-trifluoromethylpyrid-2-yloxy)phenyl)-3-(2,6-difluorobenzoyl)urea], Teflubenzuron [1-(3,5-dichloro-2,4-difluorophenyl)-3-(2,6-difluorobenzoyl)urea] and Fulphenoxron [1-(4-(2-chloro-4-trifluoromethylphenoxy)-2-fluorophenyl)-3-(2,6-difluorobenzoyl)urea], formamidine derivatives such as Amitraz [N'-(2,4-dimethylphenyl)-N-((2,4-dimethylphenyl)imino)-methyl)-N-methylmethanimidamide] and Chlordimeform [N'-(4-chloro-2-methylphenyl)-N,N-dimethylmethanimidamide], thiourea derivatives such as Diafenthiuron [N-(2,6-diisopropyl-4-phenoxyphenyl)-N'-t-butylthiourea]; Fipronyl (5-amino-1-(2,6-dichloro-α,α,α-trifluoro-p-tolyl)-4-trifluoromethylsulfinyl-pyrazole-3-carbonitrite, Bromopropylate [isopropyl 4,4'-diromobenzilate], Tetradifon [2,4,4',5-tetrachlorodiphenylsulfone], Quinomethionate [6-methyl-2-oxo-1,3-dithiolo-(4,6-b)quinoxaline], Propargite [2-(4-(1,1-dimethylethyl)phenoxy)cyclohexyl 2-propynylsulfite], Fenbutatin oxide [bis(tris(2-methyl-2phenyl-propyl)tin)oxide], Hexythiazox [(4RS,5RS)-5-(4-chlorophenyl)-N-chlorohexyl-4-methyl-2-oxo-1,3-thiazolidine-3-carboxamide], Chlofentezine [3,6-bis(2-chlorophenyl)-1,2,4,5-tetrazine], Pyridaben [2-t-butyl-5-(4-t-butylbenzylthio)-4-chloropyridazin-3(2H)-one], Phenpyroxymate [t-butyl(E)-4-((1,3-dimethyl-5-phenoxypyrazol-4-yl)methyleneaminooxymethyl)benzoate], Debphenpyrad [N-4-t-butylbenzyl)-4-chloro-3-ethyl-1-methyl- 5-pyrazol carboxamide], polynactin complexes including tetranactin, trinactin and dinactin; Milbemectin, Avermectin, Ivermectin, Azadilactin [AZAD] and Pyrimidifen[5-chloro-N-(2-(4-(2-ethoxyethyl)-2,3-dimethylphenoxy)ethyl)-6-ethylpyrimidine-4-amine].

When the present compound is applied as an active ingredient of insecticides, nematocides or acaricides for agricultural use, the amount of application is usually 1 to 1,000 g or more preferably 10 to 100 g per 1,000m$^2$. Emulsifiable concentrates, wettable powders or flowable concentrates of the present compound are diluted with water to the concentration of 10 to 1,000 ppm. Granules or dusts are not diluted but used as prepared. When the present compound is applied as an active ingredient of insecticides or acaricides for domestic use, wettable powders, flowables and emulsifiable concentrates are diluted with water to the concentration of 0.01 to 10,000 ppm. Oil solutions, aerosols, fumigants, ULV agents, and poisonous baits are used as prepared.

The amount and concentration for application may be changed optionally according to the type of the formulations, time, place and method of application, the type of noxious organisms and the damage.

The invention will be further illustrated according to the production examples, formulation examples and biological test examples although the invention is not limited in any sense to these examples.

Production examples of the present compound will be described first.

EXAMPLE 1

0.62 Gram of O-methyl N-cyanomethyl carbamate was added to a solution of 271 mg of sodium hydride (60% oil dispersion) in tetrahydrofuran (50 ml) with stirring at ambient temperature. After the evolution of hydrogen gas ceased, a solution of 1.18 g of O-ethyl S-sec-butylchlorophosphate in 5 ml of tetrahydrofuran was added to the mixture, and refluxed by heating for two hours. Then tetrahydrofuran was removed under reduced pressure and the residue was extracted with chloroform. The chloroform layer was washed with water and dried over anhydrous magnesium sulfate. The magnesium sulfate was filtered off, and the filtrate was concentrated. The residue was subjected to silica gel column chromatography to yield 475 mg of O-ethyl S-sec-butyl N-cyanomethyl N-methoxycarbonyl phosphoroamidothiolate (Compound 9).

EXAMPLE 2

1.18 Grams of O-ethyl S-sec-butyl N-cyanomethylphosphoroamidothiolate was added to a solution of 0.22 g of sodium hydride (60% oil dispersion) in tetrahydrofuran (50 ml) with stirring at ambient temperature. After the evolution of hydrogen gas ceased, 0.78 g of phenyl chlorocarbonate was added to the mixed solution, and refluxed upon heating for one hour. Tetrahydrofuran was removed under reduced pressure, and the residue was subjected to the same post-treatment as the example 1 described above to yield 270 mg of O-ethyl S-sec-butyl N-cyanomethyl N-phenoxycarbonyl phosphoroamidothiolate (Compound 14).

Table 2 shows exemplified compounds produced by the invention. Substituents of the compound of the formula II are listed.

TABLE 2

Compounds of the formula II and their physical constant

| Compound No. | $R_1$ | $R_2$ | $R_3$ | n | Refrative Index | |
|---|---|---|---|---|---|---|
| 1 | $CH_3$ | $n-C_3H_7$ | $OCH_3$ | 1 | $n_D^{24.4}$ | 1.4779 |
| 2 | $CH_3$ | $n-C_3H_7$ | $OC_2H_5$ | 1 | $n_D^{23}$ | 1.4691 |
| 3 | $CH_3$ | $n-C_3H_7$ | $OC_3H_7$-i | 1 | $n_D^{21.4}$ | 1.4680 |
| 4 | $CH_3$ | $s-C_4H_9$ | $OCH_3$ | 1 | $n_D^{24}$ | 1.4812 |
| 5 | $CH_3$ | $n-C_3H_7$ | $SCH_3$ | 2 | $n_D^{23.5}$ | 1.5234 |
| 6 | $CH_3$ | $s-C_4H_9$ | $OC_2H_5$ | 1 | $n_D^{24}$ | 1.4724 |
| 7 | $C_2H_5$ | $n-C_3H_7$ | $OCH_3$ | 1 | $n_D^{24}$ | 1.4766 |
| 8 | $C_2H_5$ | $n-C_3H_7$ | $OC_2H_5$ | 1 | $n_D^{24}$ | 1.4689 |
| 9 | $C_2H_5$ | $s-C_4H_9$ | $OCH_3$ | 1 | $n_D^{22}$ | 1.4742 |
| 10 | $C_2H_5$ | $s-C_4H_9$ | $OC_2H_5$ | 1 | $n_D^{21}$ | 1.4720 |
| 11 | $C_2H_5$ | $s-C_4H_9$ | $SCH_3$ | 1 | $n_D^{21}$ | 1.5100 |
| 12 | $C_2H_5$ | $s-C_4H_9$ | $SC_3H_7$-n | 1 | $n_D^{25}$ | 1.5023 |
| 13 | $C_2H_5$ | $s-C_4H_9$ | $SCH_3$ | 2 | $n_D^{22.1}$ | 1.5162 |
| 14 | $C_2H_5$ | $s-C_4H_9$ | $OC_6H_5$ | 1 | $n_D^{22}$ | 1.5162 |
| 15 | $CH_3$ | $s-C_4H_9$ | $OC_6H_5$ | 1 | $n_D^{24.5}$ | 1.5037 |
| 16 | $C_2H_5$ | $s-C_4H_9$ | $C_6H_5$ | 1 | $n_D^{24}$ | 1.5101 |
| 17 | $C_2H_5$ | $s-C_4H_9$ | $OC_3H_7$-i | 1 | $n_D^{23}$ | 1.4662 |
| 18 | $C_2H_5$ | $s-C_4H_9$ | $OC_4H_9$-i | 1 | $n_D^{24}$ | 1.4683 |
| 19 | $C_2H_5$ | $s-C_4H_9$ | $SC_3H_7$-n | 2 | $n_D^{23}$ | 1.5055 |
| 20 | $C_2H_5$ | $s-C_4H_9$ | $OC_2H_5$ | 2 | $n_D^{25}$ | 1.4721 |

Formulation examples are described next. In the description below, part(s) represents part(s) by weight.

Formulation Example 1 Emulsifiable Concentrates

Ten parts of each of the compounds 1 to 20 are dissolved in 35 parts of xylene and 35 parts of dimethylformamide, then mixed with 14 parts of polyoxyethylene styrylphenyl ether and 6 parts of calcium dodecylbenzenesulfonate, and stirred sufficiently to give 10% emulsifiable concentrate for each compound.

Formulation Example 2 Wettable Powders

Twenty parts of each of the compounds 1 to 20 are added to a mixture of 4 parts of sodium dodecyl sulfate, 2 parts of lignin calcium sulfonate, 20 parts of synthetic hydrated silicon hydroxide fine powder and 54 parts of diatomaceous earth, and then stirred with a mixer to give 20% wettable powders for each compound.

Formulation Example 3 Granules

Five parts of each of the compounds 1 to 20 are separately mixed with a mixture of 5 parts of sodium dodecylbenzenesolfonate, 30 parts of bentonite and 60 parts of clay, and then the resultant mixture is stirred sufficiently. The mixture is further mixed with an appropriate amount of water, stirred sufficiently, granulated with a granulator, and air-dried to give 5% granules for each compound.

Formulation Example 4 Dusts

One part of each of the compounds 1 to 20 separately dissolved in an appropriate amount of acetone is mixed with 5 parts of synthetic hydrated silicon hydroxide fine powder, 0.3 part of PAP and 93.7 parts of clay, and then stirred with a mixer to give 1% dusts for each compound.

Formulation Example 5 Flowables (Water-based Emulsions)

Ten parts of each of the present compounds 1 to 20 are added to a solution of 6 parts of polyvinyl alcohol in 40 parts of water, and the resultant mixture is stirred with a mixer to give a dispersion. The dispersion is mixed with a solution of 0.05 part of xanthan gum and 0.1 part of aluminum magnesium silicate in 40 parts of water, and then with 10 parts of propylene glycol and slowly stirred to give 10% water-based emulsion for each compound.

Formulation Example 6 Oil Solutions 0.1 Part of each of the present compounds 1 to 20 is dissolved in 5 parts of xylene and 5 parts of trichloroethane and the solution is mixed with 89.9 parts of deodorized kerosine to give 0.1% oil solutions for each compound.

Formulation Example 7 Oil-based Aerosols

Each oil aerosol is obtained by filling an aerosol vessel with a mixture of 0.1 part of each of the present compounds 1 to 20, 0.2 part of tetramethrin, 0.1 part of d-phenothrin, 10 parts of trichloroethane, and 59.6 parts of deodorized kerosene, and the vessel is set up with a valve through which 30 parts of a propellant (liquefied petroleum gas) are charged under pressure.

Formulation Example 8 Water-based Aerosols

An aerosol vessel is filled with 50 parts of pure water and a mixture of 0.2 part of each of the present compounds 1 to 20, 0.2 part of d-allethrin, 0.2 part of d-phenothrin, 5 parts of xylene, 3.4 parts of deodorized kerosine and 1 part of an emulsifier Atmos 300 (registered trade mark by Atlas Chemical), and the aerosol vessel is fixed up with a valve, through which 40 parts of a propellant(liquefied petroleum gas) are charged under pressure.

The following biological tests were conducted to demonstrate that each compound of the invention works as an excellent active ingredient of an insecticide, a nematocide or an acaricide while having rather low acute toxicity to mammals. In the description below, the present compounds are shown by the numbers in Table 2 whereas a compound used as a control is shown by the symbol in Table 3.

TABLE 3

| Compound Symbol | Chemical structure | Remarks |
|---|---|---|
| A | $CH_3O$, $O$ <br> $\phantom{xxx}\backslash\parallel$ <br> $\phantom{xxxxx}P$—$NHCH_3$ <br> $\phantom{xx}/$ <br> sec-$C_4H_9S$ | Compound No. 5 disclosed in Japanese Patent KOKAI No. 59-108796 |

Biological Test 1 Insecticidal Activity Against Larvae of *Spodoptera litura*

Emulsifiable concentrates were prepared for each of the present compounds according to the formulation example 1. Thirteen grams of artificial bait for *Spodoptera litura* were placed in a polyethylene cup (diameter: 11 cm) and impregnated with 2 ml of the emulsifiable concentrate diluted with water (500 ppm). Ten 4-instar larvae of *Spodoptera litura* were put in the polyethylene cup. After six days, the mortality of the larvae was examined. The results are shown in Table 4.

TABLE 4

| Activity against larvae of *Spodoptora litura* | |
|---|---|
| Compound | Mortality (%) |
| 1 | 100 |
| 2 | 100 |
| 3 | 100 |
| 4 | 100 |
| 5 | 100 |

TABLE 4-continued

| Activity against larvae of Spodoptora litura | |
|---|---|
| Compound | Mortality (%) |
| 6 | 100 |
| 7 | 100 |
| 8 | 100 |
| 9 | 100 |
| 10 | 100 |
| 11 | 100 |
| 12 | 100 |
| 13 | 100 |
| 14 | 100 |
| 16 | 100 |
| 17 | 100 |
| 18 | 100 |
| 20 | 100 |
| untreated | 0 |

Biological Test 2 Insecticidal Activity Against Larvae of Nilaparvata lugens

A stalk of a rice plant was dipped for one minute in a 500 ppm aqueous solution obtained by diluting each emulsifiable concentrate prepared from each of the present compounds according to the formulation example 1 and then air-dried. The rice plant stalk was placed in a polyethylene cup (diameter: 5.5 cm) where filter paper (diameter: 5.5 cm) impregnated with 1 ml of water was put. Approximately 30 larvae of Nilaparvata lugens were put in the polyethylene cup. After six days, the activity was evaluated according to the following criteria:

A: no living larvae
B: the number of the living larvae is not greater than 5
C: the number of the living larvae is 6 or more The results are shown in Table 5.

TABLE 5

| Activity against larvae of Nilaparvata lugens | |
|---|---|
| Compound | Activity |
| 1 | A |
| 2 | A |
| 3 | A |
| 4 | A |
| 6 | A |
| 7 | A |
| 8 | A |
| 14 | A |
| 16 | A |
| 17 | A |
| 18 | A |
| untreated | C |

Biological Test 3 Insecticidal Avtivity Against Blattella germanica

Filter paper of 5.5 cm in diameter was laid in the bottom of a polyethylene cup (diameter: 5.5 cm). After 0.7 ml of a 500 ppm aqueous solution obtained by diluting each emulsifiable concentrate prepared from each of the present compounds according to the formulation example 1 was dropped on the filter paper and approximately 30 mg of sucrose was uniformly scattered and put on the filter paper as bait, ten male cockroaches (Blattella germanica) were left in the cup with a cover. After one day, the mortality was examined for the cockroaches.

Table 6 shows the results.

TABLE 6

| Activity against Blattella germanica | |
|---|---|
| Compound | Mortality (%) |
| 1 | 100 |
| 2 | 100 |
| 3 | 100 |
| 4 | 100 |
| 6 | 100 |
| 7 | 100 |
| 8 | 100 |
| 9 | 100 |
| 10 | 100 |
| 11 | 100 |
| 12 | 100 |
| 13 | 100 |
| 14 | 100 |
| 16 | 100 |
| 17 | 100 |
| 18 | 100 |
| 19 | 100 |
| 20 | 100 |
| untreated | 0 |

Biological Test 4 Insecticidal Activity Against Musca domestica

Filter paper of 5.5 cm in diameter was laid in the bottom of a polyethylene cup (diameter: 5.5 cm). After 0.7 ml of a 500 ppm aqueous solution obtained by diluting each emulsifiable concentrate prepared from each of the present compounds according to the formulation example 1 was dropped on the filter paper and approximately 30 mg of sucrose was uniformly scattered, and put on the filter paper as bait, ten female house flies (Musca domestica) were left in the cup with a cover. After one day, the mortality was examined for the flies.

Table 7 shows the results.

TABLE 7

| Activity against Musca domestica | |
|---|---|
| Compound | Mortality (%) |
| 1 | 100 |
| 2 | 100 |
| 3 | 100 |
| 4 | 100 |
| 5 | 100 |
| 6 | 100 |
| 7 | 100 |
| 8 | 100 |
| 9 | 100 |
| 10 | 100 |
| 11 | 100 |
| 12 | 100 |
| 13 | 100 |
| 14 | 100 |
| 16 | 100 |
| 17 | 100 |
| 18 | 100 |
| 19 | 100 |
| 20 | 100 |
| untreated | 0 |

Biological Text 5 Insecticidal Activity Against Larvae of Diabrotica undecimpunctata Filter paper of 5.5 cm in diameter was laid in the bottom of a polyethylene cup (diameter: 5.5 cm). After 1 ml of a 50 ppm aqueous solution obtained by diluting each of the emulsifiable concentrate prepared from each of the present compounds according to the formulation example 1 was dropped on the filter paper and one sprouting corn crop was placed as bait on the paper, approximately thirty eggs of Diabrotica undecimpunctata were left on the filter paper. After eight days, the rate of hatched larvae was examined. The activity were evaluated according to the following criteria:
A: Mortality 100%
B: Mortality not less than 90% but less than 100%
C: Mortality less than 90%
The results are shown in Table 8.

TABLE 8

| Activity against larvae of Diabrotica undecimpunctata | |
|---|---|
| Compound | Activity |
| 1 | A |
| 2 | A |
| 3 | A |
| 4 | A |
| 5 | A |
| 6 | A |
| 7 | A |
| 8 | A |
| 9 | A |
| 10 | A |
| 11 | A |
| 12 | A |
| 13 | A |
| 14 | A |
| 16 | A |
| 17 | A |
| 18 | A |
| 19 | A |
| 20 | A |
| untreated | C |

Biological Test 6 Activity Against Root-knot Nematodes

One ml of a 500 ppm aqueous solution of each of the present compounds obtained by diluting each emulsifiable concentrate prepared from each of the present compounds according to the formulation example 1 was mixed with 19 g of soil contaminated with root-knot nematodes (concentration of active ingredient in soil: 25 ppm). After the soil was kept at 27° C. for 24 hours, the root of a tomato plant (approximately two weeks after sprouting) in a cup was covered with the soil and some water was given to the plant. After four weeks, damage to the root of the tomato plant was evaluated according to the following criteria:
—: substantially no root knots
+: several to ten odds root knots
++: larger number of root knots (heavier damage than +)
The results are shown in Table 9.

TABLE 9

| Activity against root-knot nematodes | |
|---|---|
| Compound | Activity |
| 1 | — |
| 2 | — |
| 3 | — |
| 4 | — |
| 5 | — |
| 6 | — |
| 7 | — |
| 8 | — |
| 9 | — |
| 10 | — |
| 11 | — |
| 12 | — |
| 13 | — |
| 14 | — |
| 16 | — |
| 17 | — |
| 18 | — |
| 19 | — |
| 20 | — |

TABLE 9-continued

| Activity against root-knot nematodes | |
|---|---|
| Compound | Activity |
| untreated | ++ |

Biological Test 7 Insecticidal Activity Against Larvae of *Culex pipiens pallens*

Each of emulsifiable concentrates prepared from each of the present compounds according to the formulation example 1 was diluted with water, and 0.7 ml of the diluted solution was added to 100 ml of ion-exchanged water (concentration of active ingredient: 3.5 ppm). Twenty last-instar larvae of *Culex pipiens pallens* were left in the water. After one day, the activity was evaluated according to the following criteria:
A: Mortality not less than 90%
B: Mortality not less than 10% but less than 90%
C: Mortality less than 10%
The results are shown in Table 10.

TABLE 10

| Activity against Culex pipiens pallens | |
|---|---|
| Compound | Activity |
| 1 | A |
| 2 | A |
| 3 | A |
| 4 | A |
| 6 | A |
| 7 | A |
| 8 | A |
| 9 | A |
| 10 | A |
| 11 | A |
| 12 | A |
| 13 | A |
| 14 | A |
| 16 | A |
| 17 | A |
| 18 | A |
| 19 | A |
| 20 | A |
| untreated | C |

Biological Test 8 Activity Against *Tetranychus cinnabarinus*

Ten male mites (*Tetranychus cinnabarinus*) per leaf were placed on a pot-planted kidney bean (*Phasseolus vulgaris*: seven days after sowing) and kept in a thermostatic chamber. After six days, 15 ml of a 500 ppm aqueous solution obtained by diluting each emulsifiable concentrate of each of the present compounds according to the formulation example 1 was sprayed in a pot simultaneously with injection of 2 ml of the solution into soil. After eight days, damage to the plant by *Tetranychus cinnabarinus* was evaluated according to the following criteria:
—: substantially no damage
+: little damage
++: heavy damage
The results are shown in Table 11.

TABLE 11

| Activity against Tetranychus cinnabarinus | |
|---|---|
| Compound | Activity |
| 1 | — |
| 2 | — |
| 3 | — |
| 4 | — |
| 5 | — |

TABLE 11-continued

| Activity against *Tetranychus cinnabarinus* | |
|---|---|
| Compound | Activity |
| 6 | − |
| 7 | − |
| 8 | − |
| 9 | − |
| 10 | − |
| 11 | − |
| 12 | − |
| 13 | − |
| 14 | − |
| 15 | − |
| 16 | − |
| 17 | − |
| 18 | − |
| 19 | − |
| 20 | − |
| untreated | ++ |

Biological Test 9 Acute Toxicity in Oral Application to Mice

Each of the present compound was diluted with corn oil to a predetermined concentration. After subjecting the mice to a twenty-hour fasting, 0.1 ml of the diluted solution per 10 g weight was forcibly applied into the stomach of each ICR male 6-week old mouse (weight: 24 to 31 g). The mice were given food and water four hours after the application and thereafter regularly fed and watered, and kept in a cage. After seven days, the mortality was examined for the mice (4 mice/group). The results are shown in Table 12.

TABLE 12

| Comparison of acute toxicity in oral application to mice | | |
|---|---|---|
| Compound | Dosage (mg/kg) | Mortality (%) |
| 9 | 30 | 0 |
| 13 | 30 | 0 |
| A | 5 | 100 |

What is claimed is:

1. An amidothiophosphate derivative represented by the formula II:

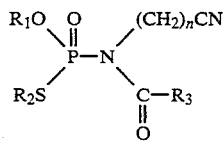

wherein $R_1$ is a methyl group or an ethyl group; $R_2$ is a n-propyl group or a sec-butyl group; $R_3$ is a $C_1$–$C_4$ alkoxy group, a $C_1$–$C_4$ alkylthio group, a phenyl group or a phenoxy group; and n represents 1 or 2.

2. An amidothiophosphate derivative according to claim 1, which is O-ethyl S-sec-butyl N-cyanomethyl N-methoxycarbonyl phosphoroamidothiolate.

3. An amidothiophosphate derivative according to claim 1, which is O-ethyl S-sec-butyl N-cyanomethyl N-phenoxycarbonyl phosphoroamidothiolate.

4. A composition for controlling insects, nematodes or acarines which comprises an effective amount of the amidothiophosphate derivative according to claim 1 and inert carriers.

5. A method of controlling insects, nematodes or acarines which comprises applying an effective amount of the amidothiophosphate derivative according to claim 1 to the locus where pests propagate.

* * * * *